United States Patent [19]
Béland et al.

[11] Patent Number: 5,658,249
[45] Date of Patent: Aug. 19, 1997

[54] MODULAR HAND-HELD DEVICE FOR USE WITH A SUCTION IRRIGATION ELECTROSURGICAL TOOL

[75] Inventors: Germain Béland; Guy Wadell, both of Sherbrooke; Jacques Poisson, Fleurimont; Fernand Jalbert, Sherbrooke, all of Canada

[73] Assignee: RD-Chus Inc., Fleurimont, Canada

[21] Appl. No.: 500,585

[22] Filed: Jul. 11, 1995

[51] Int. Cl.⁶ ............................................. A61M 1/00
[52] U.S. Cl. ........................... 604/33; 604/35; 604/21; 604/27; 604/19
[58] Field of Search ........................ 604/33, 35, 48, 604/43, 19, 27, 30, 21

[56] References Cited

U.S. PATENT DOCUMENTS

| | | | |
|---|---|---|---|
| 4,680,026 | 7/1987 | Weightman et al. | 604/33 |
| 4,708,717 | 11/1987 | Deane et al. | 604/35 |
| 5,045,055 | 9/1991 | Gonser et al. | 604/33 |
| 5,120,305 | 6/1992 | Boehringer et al. | 604/35 |
| 5,186,714 | 2/1993 | Boudreault | 604/21 |
| 5,542,918 | 8/1996 | Atkinson | 604/27 |

FOREIGN PATENT DOCUMENTS

| | | |
|---|---|---|
| 339857 | 4/1989 | European Pat. Off. . |
| 0455321 | 2/1991 | European Pat. Off. . |
| 0463363 | 5/1992 | European Pat. Off. . |
| WO9204059 | 3/1992 | WIPO . |

*Primary Examiner*—Robert A. Hafer
*Assistant Examiner*—Cris L. Rodriguez
*Attorney, Agent, or Firm*—Robic

[57] ABSTRACT

Disclosed is a modular hand-held device for use with a suction irrigation electrosurgical tool having a rear inlet/outlet port provided with an electrically conductive surface. It has a rear handle member, a middle valve member and a front member. An electrical connection device is provided for supplying electrical energy to the electrically conductive surface when the rear inlet/outlet port of the suction irrigation electrosurgical tool is received into an inlet/outlet port of the front member. A first mechanical connector is provided for removably connecting front ports of the handle member respectively to the corresponding rear ports of the middle valve member, and a second mechanical connector is provided for removably connecting an inlet/outlet front port of the middle valve member to an inlet/outlet rear port of the front member. This device can be fully dismantled, thereby making it possible to clean and sterilize all its component for further uses.

20 Claims, 4 Drawing Sheets

5,658,249

MODULAR HAND-HELD DEVICE FOR USE WITH A SUCTION IRRIGATION ELECTROSURGICAL TOOL

FIELD OF THE INVENTION

The present invention relates to a modular hand-held device for use with a suction irrigation electrosurgical tool having a rear inlet/outlet port provided with an electrically conductive means.

DESCRIPTION OF THE PRIOR ART

A plurality of prior art references are know to the applicant.

U.S. Pat. No. 5,186,714 granted on Feb. 16, 1993, of Boudreault et al. discloses a multifunctional surgical instrument for use in laparoscopic surgery. This instrument is partially modular only. Indeed, the cartridge of the apparatus, which comprises a three-way valve, cannot be dismantled in such a manner to allow cleaning and sterilization of the three-way valve. In such case, the three-way valve cannot be sterilized and must be thrown away after use.

European laid-open patent application No. 0,455,321 discloses a percutaneous laparoscopic cholecystectomy instrument. Once again, this instrument cannot be dismantled in such a way to allow a cleaning and sterilization of all its components. As a result, most of these components cannot be used again.

European laid-open patent application No. 0,463,363, discloses a tool for laparoscopic surgery. Again, this tool cannot be dismantled in such a way to allow cleaning and sterilization of all its components.

European laid-open patent application No. 0,339,857 discloses a pump with removal cartridges, and International laid-open No. WO 92/04059 discloses a surgical device of the same type. Again, none of these patent documents describes a surgical device which can be easily dismantled to allow cleaning and sterilization of all its components.

A first object of the present invention is to provide a modular hand-held device for use With a suction irrigation electrosurgical tool, which can be easily dismantled to allow efficient cleaning and sterilization thereof so that all its components can be reused for another surgical operation.

Another object of the invention is to provide a device of the above mentioned type, in which the valve-operating push-buttons are positioned in such a manner as to make the device much easier to handle, especially during gynecological operations.

A further object of the invention is to provide a device of the above type, wherein the electrical connection means of the electrosurgical component is easily adjustable at any angle, thereby making the device easy to use whatever be the position of the electric supply equipment in the surgery room.

SUMMARY OF THE INVENTION

More particularly, the present invention provides a modular hand-held device for use with a suction irrigation electrosurgical tool having a rear inlet/outlet port provided with an electrically conductive means, such device comprising:

(i) a rear handle member having a rear side and a front side, and including:
  (a) a first fluid line extending through the handle member and having a fluid inlet rear port located on the rear side, and a fluid outlet front port located on the front side; and
  (b) a first vacuum line extending through the handle member and having a vacuum inlet/outlet rear port located on the rear side, and a vacuum inlet/outlet front port located on the front side;

(ii) a middle valve member having a rear side, a front side and an inlet/outlet front port located on the front side of the valve member, and including:
  (a) a second fluid line extending through the valve member and having a fluid inlet rear port located on the rear side of the valve member, and a fluid outlet front port;
  (b) a second vacuum line extending through the valve member and having a vacuum inlet/outlet rear port located on the rear side of the valve member, and a vacuum inlet/outlet front port;
  (c) an inner mixing chamber respectively connected to the fluid outlet front port of the second fluid line, the vacuum inlet/outlet front port of the second vacuum line and the inlet/outlet front port of the valve member; and
  (d) first and second valve units located respectively along the second fluid and vacuum lines, each having a blocking means movable from a rest position where the corresponding line is blocked to an operating position where the corresponding line is free, and a push-button adjacent to the handle member for moving the corresponding blocking means from its rest position to its operating position and vice versa;

(iii) a front member having a rear side and a front side, provided with:
  (a) a channel extending through the front member and having an inlet/outlet rear port located on the rear side of the front member, an inlet/outlet front port located on the front side of the front member, the inlet/outlet front port of the channel being for receiving the rear inlet/outlet port of the suction irrigation electrosurgical tool; and
  (b) an electrical connection means having an outer electrical terminal for receiving electrical energy and an inner electrical terminal for connection to the electrically conductive means when the rear inlet/outlet port of the suction irrigation electrosurgical tool is received into the second inlet/outlet port of the front member;

(iv) a first mechanical connecting means for removably connecting the front ports of the handle member respectively to the corresponding rear ports of the middle valve member; and (v) second mechanical connecting means for removably connecting the inlet/outlet front port of the middle valve member to the inlet/outlet rear port of the front member.

Preferably, the push-buttons are adjacent and located on both sides of a central longitudinal axis of the handle member. This feature makes the device particularly useful for gynecological operations.

A non-restrictive description of a preferred embodiment will now be given with reference to the appended drawings.

DESCRIPTION OF A PREFERRED EMBODIMENT

Figure 1:
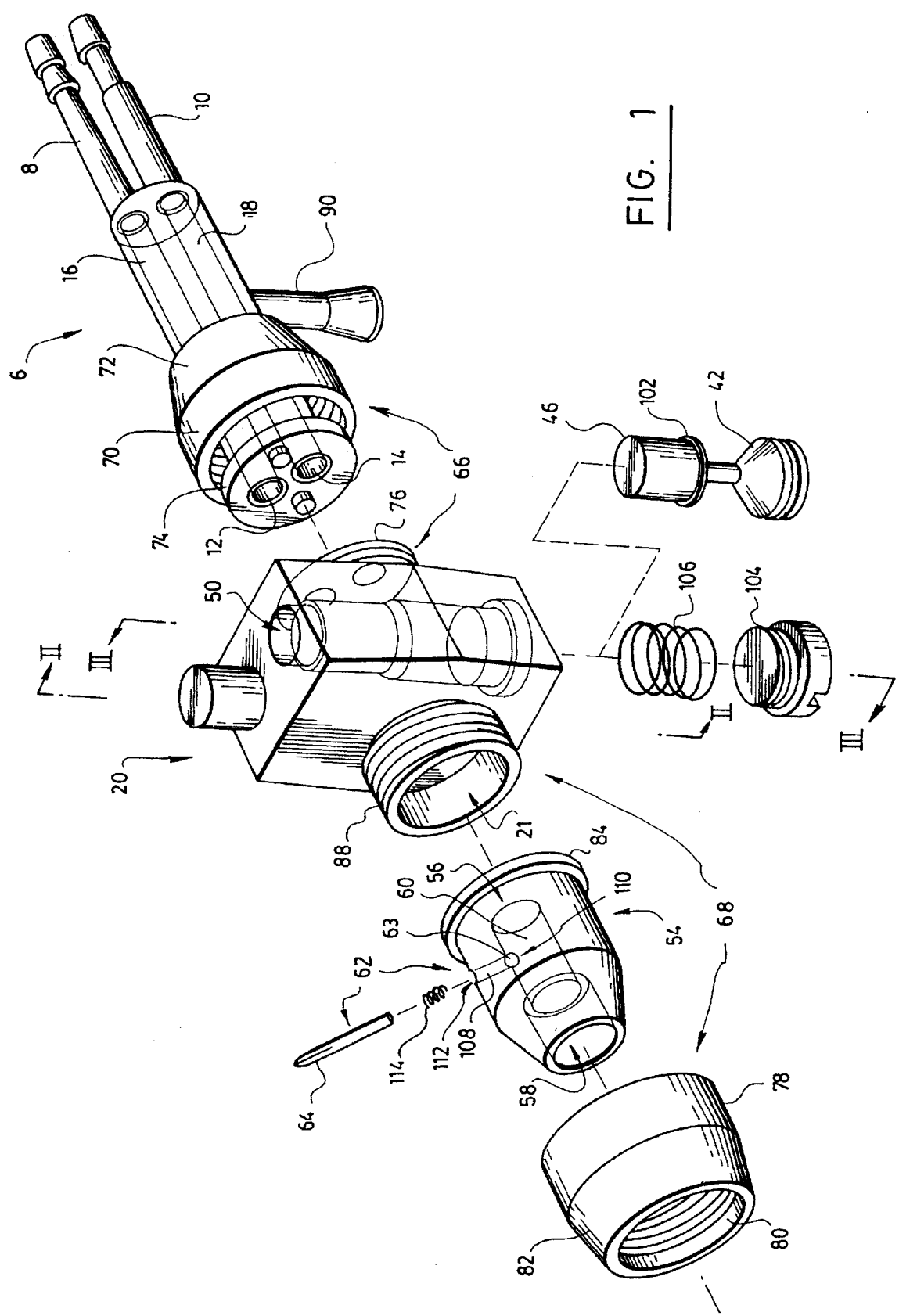
FIG. 1 is a perspective exploded view of a modular hand-held device according to the present invention.
Figure 2:
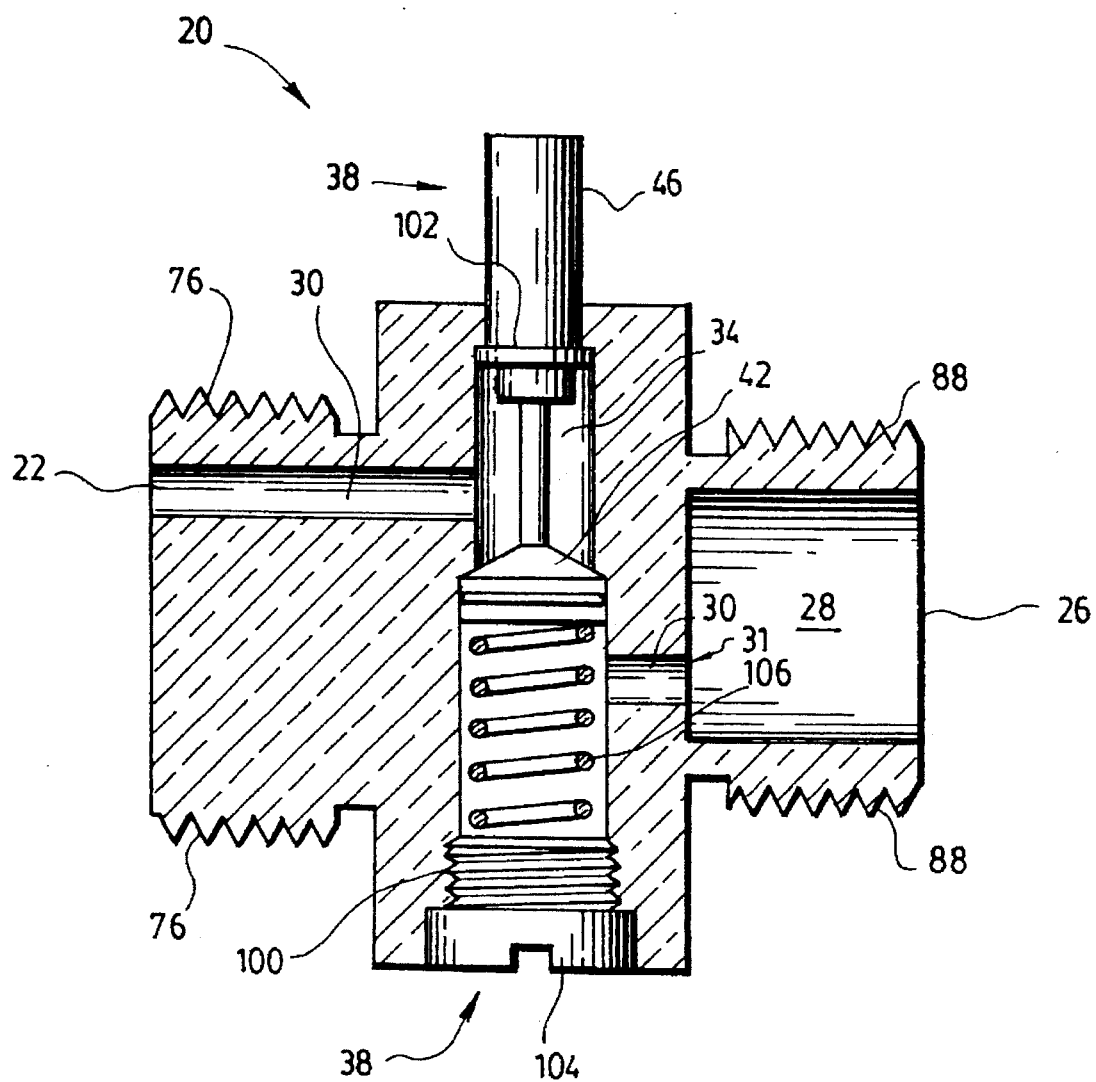
FIG. 2 is a cross section view along line II—II of FIG. 1.
Figure 3:
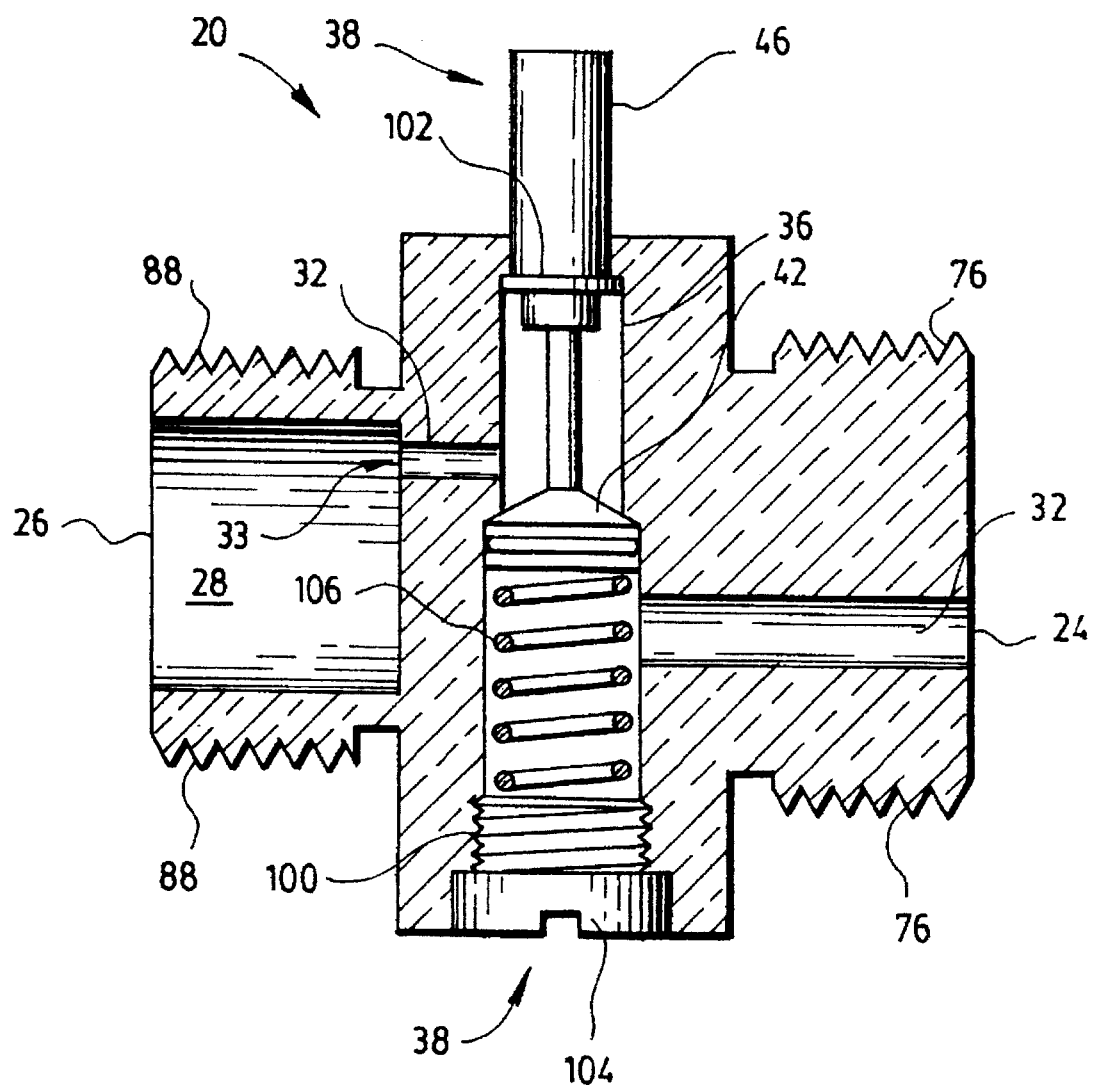
FIG. 3 is a cross section view along lines III—III of FIG. 1.
Figure 4:
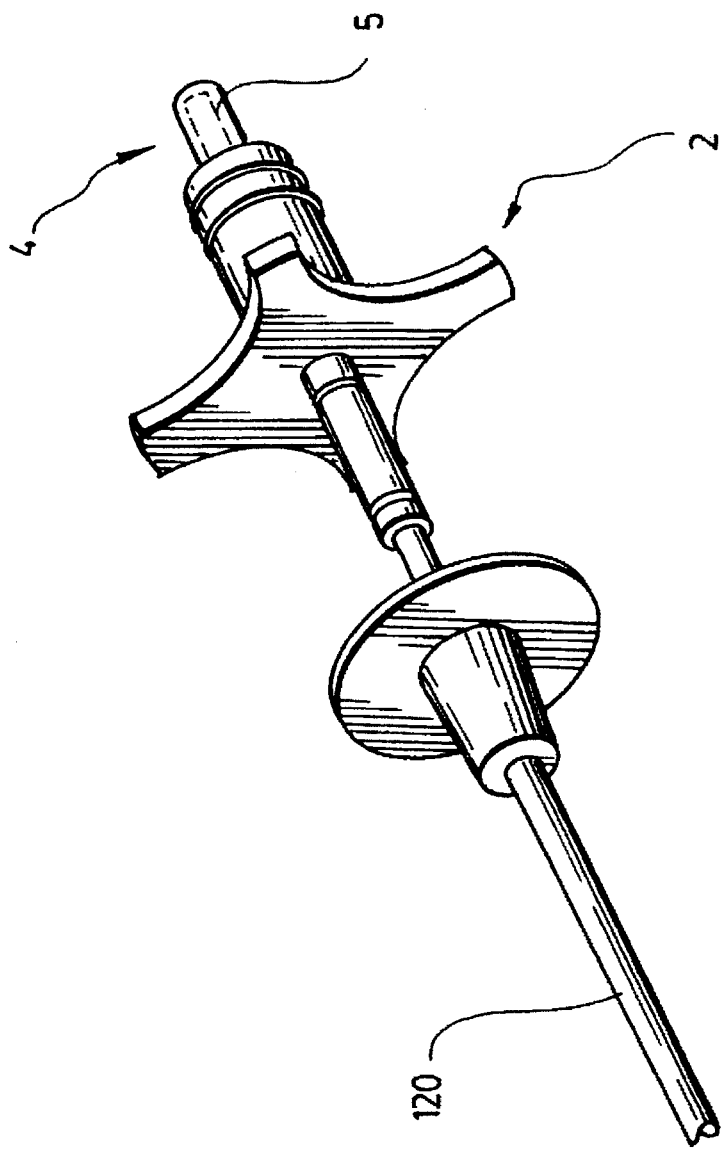
FIG. 4 is a perspective view of a suction irrigation electrosurgical tool.

FIGS. 1 to 3 show a modular hand-held device according to the invention, for use with a suction irrigation electrosurgical tool 2, shown in FIG. 4. The tool 2 which is known per se (see for example, U.S. Pat. No. 5,186,714), has a rear inlet/outlet port 4 provided with an electrically conductive surface 5.

The modular hand-held device according to the invention comprises a rear handle member 6 having a rear side and a front side. The handle member 6 includes a first fluid line 16 extending through the handle member 6. A fluid inlet rear port 8 is located on the rear side. A fluid outlet front port 12 is located on the front.

The handle member 6 also includes a first vacuum line 18 extending through the handle member 6. A vacuum inlet/outlet rear port 10 is located on the rear side. A vacuum inlet/outlet front port 14 is located on the front side.

The device also comprises a middle valve member 20 having a rear side, a front side and an inlet/outlet front port 26 located on its front side. The valve member 20 includes a second fluid line 30 extending through the valve member 20. A fluid inlet rear port 22 is located on the rear side. A fluid outlet front port 31 is also provided.

A second vacuum line 32 extends through the valve member 20. It has a vacuum inlet/outlet rear port 24 located on the rear side of the valve member, and a vacuum inlet/outlet front port 33.

An inner mixing chamber 28 is respectively connected to the fluid outlet front port 31 of the second fluid line 30, to the vacuum inlet/outlet front port 33 of the second vacuum line 32 and to the inlet/outlet front port 26 of the valve member 20. First and second valve units 38 are located respectively along the second fluid and vacuum lines 30 and 32. Each valve unit 38 has a plug member 42 movable from a rest position where the corresponding line 30 or 32 is blocked to an operating position where the corresponding line 30 or 32 is free. Each valve unit has also a push-button 46 adjacent to the handle member 6 for moving the corresponding plug member 42 from its rest position to its operating position and vice versa.

The device also comprises a front member 54 having a rear side and a front side. The front member 54 is provided with a channel 60 extending through the front member 54. An inlet/outlet rear port 56 of the channel 60 is located on the rear side of the front member 54. An inlet/outlet front port 58 of the channel 60 is located on the front side of the front member 54. The inlet/outlet front port 58 is for receiving the rear inlet/outlet port 4 of the suction irrigation electrosurgical tool 2.

An electrical connection means 62 is provided. It has an outer electrical terminal 64 for receiving electrical energy and an inner electrical terminal 63 for connection to the electrically conductive surface 5 when the rear inlet/outlet port 4 of the suction irrigation electrosurgical tool 2 is received into the second inlet/outlet port 58 of the front member 54.

A first mechanical connector 66 is provided for removably connecting the front ports 12 and 14 of the handle member 6 respectively to the corresponding rear ports 22 and 24 of the middle valve member 20. A second mechanical connector 68 is provided for removably connecting the inlet/outlet front port 21 of the middle valve member 20 to the inlet/outlet rear port 56 of the front member 54.

The modular hand-held device described above can be easily dismantled by means of the first and second connectors 66 and 68 to allow efficient cleaning and sterilizing of all of its components. Because of that, the rear handle member 6, the middle valve member 20 and the front member 54 can be used for a future surgical operation.

The handle member 6 is substantially cylindrical. The first mechanical connector 66 comprises a ring 70 having an inner threaded surface with an appropriate diameter to slide along the handle member 6. The ring 70 has a first inner diameter section which is wider on one side thereof and a second inner diameter section which is narrower on the opposite side 72 thereof.

A cylindrical collar 74 is located around the fluid outlet and vacuum inlet/outlet front ports 12 and 14 and integral with the handle member 6. The collar 74 has an outer diameter which is smaller than the first inner diameter section of the ring 70 and bigger the second inner diameter section located on the side 72.

A cylindrical threaded surface 76 is provided around the rear ports 22 and 24 of the middle valve member 20 and is integral with the middle valve member 20. It can be seen that the handle member 6 can be easily connected to or disconnected from the valve member 20 by means of the connector 66.

The front member 54 is substantially cylindrical. The second mechanical connector 68 comprises a ring 78 having an inner threaded surface with an appropriate diameter to slide along the front member 54.

The ring 78 has a first inner diameter section which is wider on one side thereof and a second inner diameter section 80 which is narrower on the opposite side 82 thereof.

A cylindrical collar 84 is located around the first inlet/outlet port 56 of the front member 54 and is integral with the front member 54. The collar 84 has an outer diameter which is smaller than the first inner diameter section and bigger the second inner diameter section 80.

A cylindrical threaded surface 88 is provided around the front port 26 of the middle valve member 20 and is integral with the middle valve member 20. It can be seen that the valve member 20 can be easily connected to or disconnected from the front member 54 by means of the connector 68. It is worth noting that connectors different from the one shown in the figures can be used.

Preferably, the handle member 6 is provided on its outer periphery along its length with a stop 90 for positioning a hand of the user. The push-buttons 46 are adjacent and located, when in operative position, on both sides of a central longitudinal axis of the handle member 6. The push-buttons 46 and the stop 90 face respectively opposite parallel directions when the handle member 6 is mechanically connected to the valve member 20.

The middle valve member 20 is provided with first and second separate bores 34 and 36 respectively transversal to the second fluid and vacuum lines 30 and 32. The first and second valve units 38 are respectively located in the first and second separate bores 34 and 36. The first and second valve units 38 are spring-biased valve units 38.

Each of the bores 34 and 36 has a substantially constant cross section along its length, an upper opening 50 with a cross section narrower than the one of the corresponding bore 34 or 36 to provide a stop, and a lower opening provided with threads 100. Each of the push-buttons 46 has a cross section for sliding through the upper opening 50 of the corresponding bore 34 or 36.

Each plug member 42 which forms a blocking means has dimensions for sliding along the corresponding bore 34 or 36. Each of the spring-biased valve units 38 further comprises a collar 102 having a side connected to a lower end of the corresponding push-button 46 to rest against the stop of the corresponding upper opening 50, and an opposite side connected to the corresponding plug member 42. Screws 104 are provided respectively for blocking the lower opening of the corresponding bores 34 and 36. In each of the bores 34 and 36, a spring 106 is located, when in operative position, between the corresponding plug member 42 and screw 104 for biasing the plug member 42.

The front member 54 is provided with a radial bore 108 extending from the channel 60 of the front member 54 to the periphery thereof. The radial bore 108 has an inner extremity provided with an opening 110 of reduced cross section to provide an inner stop, and an outer extremity 112.

The inner electrical terminal is a steel ball 63 located within the radial bore 108. The outer electrical terminal is a metal rod 64 insertable into the outer extremity 112 of the radial bore 108 and lockable therein. The electrical connection means further comprises a metal spring 114 located, when in operative position, between the steel ball 63 and an inner end of the metal rod 64 to bias the steel ball 63 against the inner stop.

A suction irrigation electrosurgical tool shown in FIG. 4 is made specifically for gynecologic use. Referring now to all of the figures, in use, the handle member 6 is connected to the valve member 20 by means of connector 66 and the valve member 20 is connected to the front member 54 by means of connector 68. Then, the port 8 is connected to a fluid providing apparatus (not shown), and the port 10 is connected to a vacuum apparatus (not shown). The tool 2 is then connected to the port 58 of the front member 54. An electrical connection is established from the conducting surface 5 to an electrical supplying means (not shown) via the electrical connection means 62. The supplying of electrical energy is controlled by the operator by means of a pedal, as known in the art.

The tubular element 120 can now be inserted into the vagina of a patient by the operator. When the extremity of the tubular element 120 has reached the appropriate position inside the patient, the operator can perform a surgical operation. He or she controls electrical currents supplied to an electrode (not shown) located at the extremity of the tubular element 120 by means of a pedal, as it is known in the art. He or she can also supply fluid to the location where the surgery is performed by means of one of the push-buttons 46, and alternately he or she can also suck up fluid from the location where the surgery is performed by means of the other push-buttons 46.

When the operation is over, the handle member 6 is dismantled from the valve member 20, and the front member 54 is dismantled from the valve member 20. Also, the valve unit 38 can be removed from the valve member 20 by unscrewing the screws 104. It can be seen that all of the elements of the modular hand-held can now be properly cleaned and sterilized to be used for a future surgical operation.

Although a preferred embodiment of the invention has been described in detail herein and illustrated in the accompanying drawings, it is to be understood that the invention is not limited to this precise embodiment and that various changes and modifications may be effected therein without departing from the scope or spirit of the invention.

We claim:

1. A modular hand-held device for use with suction irrigation electrosurgical tool having a rear inlet/outlet port provided with an electrically conductive means, comprising:

(i) a rear handle member having a rear side and a front side, and including:
      (a) a first fluid line extending through the rear handle member and having a fluid inlet rear port located on the rear side, and a fluid outlet front port located on the front side; and
      (b) a first vacuum line extending through the rear handle member and having a vacuum inlet/outlet rear port located on the rear side, and a vacuum inlet/outlet front port located on the front side;

(ii) a middle valve member having a rear side, a front side and an inlet/outlet front port located on the front side, of the middle valve member, and including:
      (a) a second fluid line extending through the middle valve member and having a fluid inlet rear port located on the rear side of the middle valve member, and a fluid outlet front port;
      (b) a second vacuum line extending through the middle valve member and having a vacuum inlet/outlet rear port located on the rear side of the middle valve member, and a vacuum inlet/outlet front port;
      (c) an inner mixing chamber respectively connected to the fluid outlet front port of the second fluid line, to the vacuum inlet/outlet front port of the second vacuum line and to the inlet/outlet front port of the middle valve member; and
      (d) first and second valve units located respectively along the second fluid and vacuum lines, each having a blocking means movable from a rest position where the corresponding line is blocked to an operating position where the corresponding line is free, and a push-button adjacent to the rear handle member for moving the corresponding blocking means from its rest position to its operating position and vice versa;

(iii) a front member having a rear side and a front side, provided with:
      (a) a channel extending through the front member and having an inlet/outlet rear port located on the rear side of the front member, an inlet/outlet front port located on the front side of the front member, the inlet/outlet front port of the channel being for receiving the rear inlet/outlet port of the suction irrigation electrosurgical tool; and
      (b) an electrical connection means having an outer electrical terminal for receiving electrical energy and an inner electrical terminal for connection to the electrically conductive means when the rear inlet/outlet port of the suction irrigation electrosurgical tool is received into the second inlet/outlet port of the front member;

(iv) a first mechanical connecting means for removable connecting the front ports of the rear handle member respectively to the corresponding rear ports of the middle valve member; and (v) a second mechanical connecting means for removable connecting the inlet/outlet front port of the middle valve member to the inlet/outlet rear port of the front member.

2. A device according to claim 1, wherein the rear handle member is substantially cylindrical, and wherein the first mechanical connecting means comprises:

a ring having an inner threaded surface with an appropriate diameter to slide along the rear handle member, the ring having a first inner diameter section which is wider on one side thereof and a second inner diameter section which is narrower on an opposite side thereof;

a cylindrical collar located around the fluid outlet and vacuum inlet/outlet front ports and integral with the rear handle member, the cylindrical collar having an outer diameter which is smaller than the first inner diameter section and bigger the second inner diameter section; and a cylindrical threaded surface provided around the fluid inlet rear port and the vacuum inlet/outlet rear port, and integral with the middle valve member.

3. A device according to claim 2, wherein:

the middle valve member is provided with first and second separate bores respectively transversal to the second fluid and vacuum lines;

the first and second valve units are respectively located in the first and second separate bores; and the first and second valve units are spring-biased valve units.

4. A device according to claim 3, wherein:

each of the first and second separate bores has a substantially constant cross section along its length, an upper opening with a cross section narrower than the one of the corresponding bore to provide a stop, and a lower opening provided with threads;

each of the push-buttons has a cross section for sliding through the upper opening of the corresponding bore;

each of the blocking means is a plug member having dimensions for sliding along the corresponding bore; and each of the spring-biased valve units further comprises:
a collar having a side connected to a lower end of the corresponding push-button to rest against the stop of the corresponding upper opening, and an opposite side connected to the corresponding plug member;
a screw screwable into the threads of the lower opening of the corresponding bore; and
a spring located, when in operative position, between the corresponding plug member and screw for biasing the plug member.

5. A device according to claim 2, wherein the push buttons are adjacent and located on both sides of a central longitudinal axis of the handle member.

6. A device according to claim 5, wherein:

the rear handle member is provided on its outer periphery along its length with a stop for positioning a hand of the user; and the push-buttons and the stop face respectively opposite parallel directions when the rear handle member is mechanically connected to the middle valve member.

7. A device according to claim 2, wherein the front member is substantially cylindrical, the second mechanical connecting means comprises:

a ring having an inner threaded surface with an appropriate diameter to slide along the front member, the ring having a first inner diameter section which is wider on one side thereof and a second inner diameter section which is narrower on an opposite side thereof;

a cylindrical collar located around the first inlet/outlet port of the front member and integral with the front member, the cylindrical collar having an outer diameter which is smaller than the first inner diameter section and bigger the second inner diameter section; and a cylindrical threaded surface provided around the front port of the middle valve member and integral with the middle valve member.

8. A device according to claim 1, wherein the front member is substantially cylindrical, the second mechanical connecting means comprises:

a ring having an inner threaded surface with an appropriate diameter to slide along the front member, the ring having a first inner diameter section which is wider on one side thereof and a second inner diameter section which is narrower on an opposite side thereof;

a cylindrical collar located around the first inlet/outlet port of the front member and integral with the front member, the cylindrical collar having an outer diameter which is smaller than the first inner diameter section and bigger the second inner diameter section; and a cylindrical threaded surface provided around the front port of the middle valve member and integral with the middle valve member.

9. A device according to claim 8, wherein:

the middle valve member is provided with first and second separate bores respectively transversal to the second fluid and vacuum lines;

the first and second valve units are respectively located in the first and second separate bores; and the first and second valve units are spring-biased valve units.

10. A device according to claim 9, wherein:

each of the first and second separate bores has a substantially constant cross section along its length, an upper opening with a cross section narrower than the one of the corresponding bore to provide a stop, and a lower opening provided with threads;

each of the push-buttons has a cross section for sliding through the upper opening of the corresponding bore;

each of the blocking means is a plug member having dimensions for sliding along the corresponding bore; and each of the spring-biased valve units further comprises:
a collar having a side connected to a lower end of the corresponding push-button to rest against the stop of the corresponding upper opening, and an opposite side connected to the corresponding plug member;
a screw screwable into the threads of the lower opening of the corresponding bore; and
a spring located, when in operative position, between the corresponding plug member and screw for biasing the plug member.

11. A device according to claim 8, wherein:

the push-buttons are adjacent and located on both sides of a central longitudinal axis of the rear handle member.

12. A device according to claim 11, wherein:

the rear handle member is provided on its outer periphery along its length with a stop for positioning a hand of the user; and the push-buttons and the stop face respectively opposite parallel directions when the rear handle member is mechanically connected to the middle valve member.

13. A device according to claim 1, wherein:

the push-buttons are adjacent and located on both sides of a central longitudinal axis of the rear handle member.

14. A device according to claim 13 wherein:

the middle valve member is provided with first and second separate bores respectively transversal to the second fluid and vacuum lines;

the first and second valve units are respectively located in the first and second separate bores; and the first and second valve units are spring-biased valve units.

15. A device according to claim 13, wherein:

the front member is provided with a radial bore extending from the channel of the front member to the periphery thereof, the radial bore having an inner extremity provided with an opening of reduced cross section to provide an inner stop, and an outer extremity;

the inner electrical terminal is a steel ball located within the radial bore;

the outer electrical terminal is a metal rod insertable into the outer extremity of the radial bore and lockable therein; and the electrical connection means further comprises a metal spring located, when in operative position, between the steel ball and an inner end of the metal rod to bias the steel ball against the inner stop.

16. A device according to claim 1, wherein:

the push-buttons are adjacent and located on both sides of a central longitudinal axis of the rear handle member;

the rear handle member is provided on its outer periphery along its length with a stop for positioning a hand of the user; and the push-buttons and the stop face respectively opposite parallel directions when the rear handle member is mechanically connected to the middle valve member.

17. A device according to claim 1, wherein:

the middle valve member is provided with first and second separate bores respectively transversal to the second fluid and vacuum lines;

the first and second valve units are respectively located in the first and second separate bores; and the first and second valve units are spring-biased valve units.

18. A device according to claim 17, wherein:

each of the first and second separate bores has a substantially constant cross section along its length, an upper opening with a cross section narrower than the one of the corresponding bore to provide a stop, and a lower opening provided with threads;

each of the push-buttons has a cross section for sliding through the upper opening of the corresponding bore;

each of the blocking means is a plug member having dimensions for sliding along the corresponding bore; and each of the spring-biased valve units further comprises:

a collar having a side connected to a lower end of the corresponding push-button to rest against the stop of the corresponding upper opening, and an opposite side connected to the corresponding plug member;

a screw screwable into the threads of the lower opening of the corresponding bore; and a spring located, when in operative position, between the corresponding plug member and screw for biasing the plug member.

19. A device according to claim 17, wherein:

the front member is provided with a radial bore extending from the channel of the front member to the periphery thereof, the radial bore having an inner extremity provided with an opening of reduced cross section to provide an inner stop, and an outer extremity;

the inner electrical terminal is a steel ball located within the radial bore;

the outer electrical terminal is a metal rod insertable into the outer extremity of the radial bore and lockable therein; and the electrical connection means further comprises a metal spring located, when in operative position, between the steel ball and an inner end of the metal rod to bias the steel ball against the inner stop.

20. A device according to claim 1, wherein:

the front member is provided with a radial bore extending from the channel of the front member to the periphery thereof, the radial bore having an inner extremity provided with an opening of reduced cross section to provide an inner stop, and an outer extremity;

the inner electrical terminal is a steel ball located within the radial bore;

the outer electrical terminal is a metal rod insertable into the outer extremity of the radial bore and lockable therein; and the electrical connection means further comprises a metal spring located, when in operative position, between the steel ball and an inner end of the metal rod to bias the steel ball against the inner stop.

* * * * *